United States Patent
Amestica Salazar (10) Patent No.: US 9,808,014 B2
(45) Date of Patent: Nov. 7, 2017

(54) ACTIVE-POWDER BIOCIDAL COMPOSITION COMPRISING AT LEAST ONE COPPER SALT AND AT LEAST ONE ZINC SALT AND THE METHOD FOR THE PRODUCTION THEREOF

(75) Inventor: Luis Alberto Amestica Salazar, Comuna Providencia (CL)

(73) Assignee: Textil Copper Andino S.A. [CL/CL], Comuna Providencia (CL)

( * ) Notice: Subject to any disclaimer, the term of this patent is extended or adjusted under 35 U.S.C. 154(b) by 0 days.

(21) Appl. No.: 14/362,238

(22) PCT Filed: Dec. 16, 2011

(86) PCT No.: PCT/CL2011/000081
§ 371 (c)(1),
(2), (4) Date: Jul. 11, 2014

(87) PCT Pub. No.: WO2013/086647
PCT Pub. Date: Jun. 20, 2013

(65) Prior Publication Data
US 2014/0356404 A1    Dec. 4, 2014

(51) Int. Cl.
*A01N 59/20* (2006.01)
*A01N 59/16* (2006.01)
*D06M 16/00* (2006.01)
*D01F 1/10* (2006.01)
*C09D 5/14* (2006.01)
*A01N 25/12* (2006.01)

(52) U.S. Cl.
CPC ............. *A01N 59/20* (2013.01); *A01N 25/12* (2013.01); *A01N 59/16* (2013.01); *C09D 5/14* (2013.01); *D01F 1/103* (2013.01); *D06M 16/00* (2013.01)

(58) Field of Classification Search
CPC ........ A01N 25/12; A01N 59/16; A01N 59/20; A01N 25/10; A01N 25/34; A01N 2300/00; C09D 5/14; D01F 1/103; D06M 16/00
See application file for complete search history.

(56) References Cited

U.S. PATENT DOCUMENTS

| 5,137,569 A | 8/1992 | Waldron |
| 5,238,490 A | 8/1993 | Farmer |
| 5,298,061 A | 3/1994 | Waldron |
| 7,632,567 B1 | 12/2009 | Zhang et al. |
| 2007/0213228 A1* | 9/2007 | Zhao .................... B22F 9/24 505/430 |

FOREIGN PATENT DOCUMENTS

| ES | 2095493 | 2/1997 |
| ES | 2124319 | 2/1999 |
| ES | 2124887 | 2/1999 |
| GB | 541367 | 11/1941 |

OTHER PUBLICATIONS http://www.solubilityofthings.com/water/ion_solubility/ksp_chart.php, accessed Oct. 23, 2015, 1-6.*

* cited by examiner

Primary Examiner — Robert Cabral
(74) Attorney, Agent, or Firm — Gottlieb, Rackman & Reisman, P.C.

(57) ABSTRACT

Active-powder biocidal composition comprising at least one copper salt and at least one zinc salt such that the molar ratio between the copper salt and the zinc salt is within the range of 10 to 1 and each copper and zinc salt, separately, has a solubility constant (Kps) within the range from a value greater than or equal to $1*10-20$ to a value less than or equal to $9*10-6$. Also included is the biocidal composition that comprises the active-powder composition and a polymer, and the method for the production of said biocidal composition, which comprises: thoroughly mixing the salts in such a manner as to obtain a homogeneous distribution of an active-powder biocidal composition; controlling the mixing temperature such that it remains at approximately less than 50° C.; and mixing the resulting mixture of active powders with a polymer.

15 Claims, 1 Drawing Sheet

ACTIVE-POWDER BIOCIDAL COMPOSITION COMPRISING AT LEAST ONE COPPER SALT AND AT LEAST ONE ZINC SALT AND THE METHOD FOR THE PRODUCTION THEREOF

FIELD OF THE INVENTION

The invention relates to the controlled release of biocide agents (cations), according to the needs of speed and concentration of the biocide agents for a particular application. The invention considers the mixture of copper and zinc salts, because it has been established that copper and zinc ions enhance themselves when mutually present, increasing their biocide effect. In order for the invention to accomplish its objective, the release of biocide agents in the case of salts is defined by their solubility constant.

The invention relates to biocide compositions that include copper and zinc salts that have solubility constants (Kps) that range from values equal to or greater than $1*10^{20}$ to a value equal to or less than $9*10^{-6}$.

The current invention also relates to the method of fabrication of said compositions.

BACKGROUND OF THE INVENTION

The biocide benefits of copper salts are well documented in the literature. Upon contact with water, these salts release cuprous and/or cupric ions, depending on the type of salt. It is scientifically accepted that the mechanism through which fungus, bacteria and virus are inactivated and/or eliminated by copper ions through means of the penetration of said ions into the microorganism through the membrane. The ions that penetrate the membrane of these microorganisms alter the vital systems (membrane permeability, protein degradation, enzyme reaction inhibition, along with many other harmful effects).

Several patents document the biocide application of copper and copper salts, organic and inorganic, on polymers. Some of these applications are related to the coating of polymers with a thin layer of metal or metal salts (coating), bond formation between the polymer structure and copper ions (radicals, amino acids), and so on.

The biocide effect of zinc is also well documented. Particularly, zinc oxide has been used for a very long time as an active ingredient in dermatological formulations (creams and others) because of its properties (Sawai, 2004, Sawai J (2003) Quantitative evaluation of antibacterial activities of metallic oxide powders (ZnO, MgO and CaO) by conductimetric assay. J Microbiol Methods 54:177-182). It is also known that zinc oxide acts as a UV radiation filter.

In document JP2011052338, an antibacterial textile product is described, which has a first component that is an oxide that contains at least one of the zinc ions and copper ions and a second component, which is an oxide of at least one of the alkaline and alumina metal oxide, where at least one of the antimicrobial inorganic agents contain at least one of the components and a synthetic polyvinyl alcohol polymer merges with the textile product.

Document FR2831188 describes a woven textile product that includes a copper and/or copper compound as a fine and homogeneously dispersed powder in a polymeric material that includes, for instance and among others, vinyl chloride, vinylidenechloride. Furthermore, it also describes the production of the textile product through copper micronization and/or a copper compound in order to obtain particles smaller than 50 micrometers, by means of dispersing homogenously the particles in a polymer solution, and weaving the mixture when it is dry or moist.

Document CA2748734 describes fungicide compositions that include a copper salicylate with the formula $C_7H_4O_3Cu$ $(H_2O)_n$, where n represents 0, 1, 2 or 3; a copper hydroxide $Cu(OH)_2(H)$; a copper salt of formula $3Cu(OH)_2-X(Y)_m$, where X represents a cupric ion $Cu^{2+}$ or calcium ion $Ca^{2+}$, Y means a chloride ion $Cl^-$ or sulfate ion $SO_4^{2-}$, m is an integer number equal to 1 or 2.

In document MX2010008389 describes a wide range germicide against bacteria, virus and fungus. The invention consists of a concentrated solution of silver, copper and/or zinc ions, which is an organic vegetable solvent that has natural healing properties. The germicide can be produced by means of two major steps: A) produced through the proportional combination of two or more chemical formulas, which contains the active element or oligodynamic metals (silver, copper and zinc), such as copper gluconate, copper nitrate, copper sulfate, silver nitrate, silver oxalate, zinc nitrate, zinc gluconate, silver chloride, silver acetate, zinc sulfate or zinc oxalate; and dissolved in demineralized water and an organic stabilizer. B) Dilution in demineralized water of one of the following organic acids: maleic acid, citric acid, folic acid, oxalic acid, acetic acid, glycolic acid or any other organic acid with similar properties; the solution thus obtained recirculates through an electrolysis system.

Document GB2411405 describes a material that inhibits the growth of marine organisms on submerged surfaces, includes a copper powder dispersed on a matrix where there is also a fugitive additive included. The fugitive additive may be a volatile or water-soluble liquid or a water-soluble solid. The matrix is preferably a plastic resin such as an epoxy resin. In practice, a partially porous layer is formed with the material in order to augment the quantity of exposed copper.

The national document of the same inventors, request 134-2010, describes a method to prepare a biocide formulation from a polymeric material and an active ingredient that includes 0.1 to 40% copper, 0.1 to 40% zinc, 0.01 to 10% silver and 0.01 to 10% chitosan. The process is carried out in an anoxic atmosphere and preferably in the presence of an inert gas.

The documents disclose the state of the technique defining biocide compositions that contain copper and/or zinc ions in the presence of some polymer for specific applications. By having a single biocide composition, good use in various applications cannot be achieved, because every specific application requires a given speed and application time of the product. Besides, in the case of the biocide agents that contain salts, their release or solubilization, is defined by their solubility constant, which makes it very necessary to have biocide agents with clearly defined solubility constants.

Thus, there still exists the need of having biocide compositions specifically for the application that a given product is going to receive, that is to say they have to be developed in accordance with the use of the product.

Thus, it would be desirable to have a biocide agent suitable to be employed in different applications and that has a predefined solubility constant.

Thus, an aim of the present invention is to have a biocide composition that includes copper and zinc salts that have a solubility constant within a predefined range.

Another aim consists of having a production method of a biocide composition that includes copper and zinc salts that have a solubility constant within a predefined range.

SUMMARY OF THE INVENTION

The present invention consists of biocide compositions that include copper and zinc salts that have a solubility constant within a range that goes from a value equal to or greater than $1*10^{-20}$ until a value equal to or less than $9*10^{-6}$ and a polymer.

Besides, the present invention describes a production method of the biocide composition that includes copper and zinc salts that have a solubility constant within the previously defined range.

BRIEF DESCRIPTION OF THE DRAWINGS

It can be seen that the concentration of ions diminishes as the salts deplete and diminish and that, in the case of the total concentration (cuprous ions and zinc ions), it diminishes more rapidly, as the zinc oxide has a greater Kps value ($3.9*10^{-10}$) than the copper salts.

DETAILED DESCRIPTION OF THE INVENTION

Figure 1:
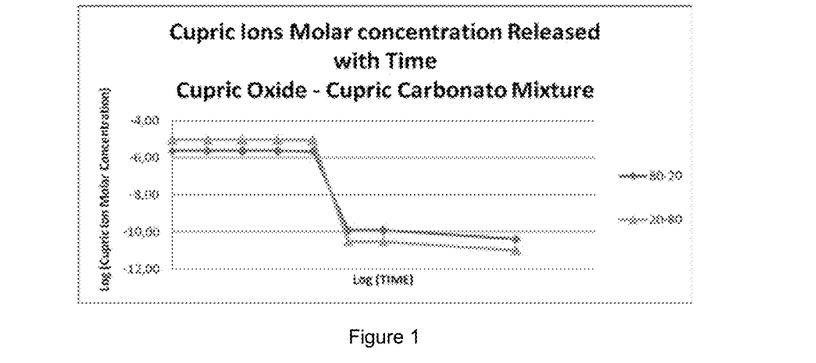
FIG. 1 shows the chart that models the concentration of cupric ions in solution through time. The simulation represents the concentration of cupric ions released by a mixture of cupric oxide and cupric carbonate, balanced in an aqueous solution in permanent renewal (washing). The curves of the chart represent: ◇ : 80% molar cupric oxide and 20% molar cupric carbonate. Δ: 20% molar cupric oxide and 80% molar cupric carbonate. It follows from the chart that as the cupric carbonate has a greater solubility product value (Kps=$1.4*10^{-10}$) than the cupric oxide (Kps=$2.2*10^{-20}$), it releases cupric ions faster. Therefore, the mixture that contains a greater molar concentration of cupric carbonate releases more ions initially, until the carbonate ions are depleted and the moment comes where the salt of less Kps value controls the concentration of released ions.
Figure 2:
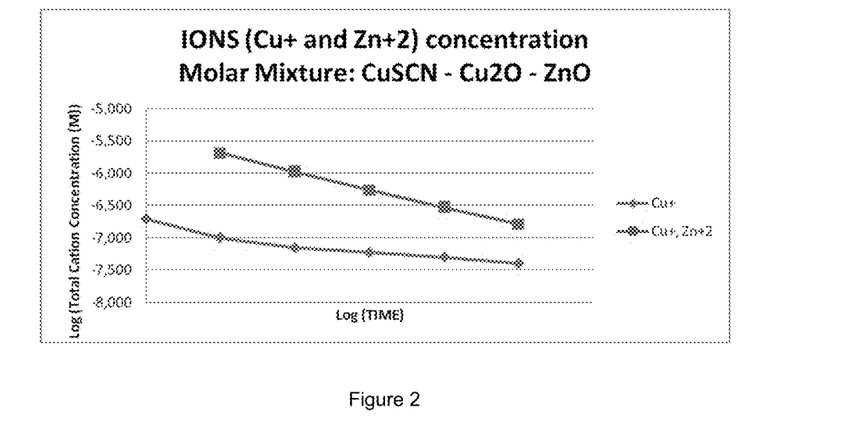
FIG. 2 shows the chart of the concentration of biocide ions (copper and zinc) released through time given the Kps values and molar percentages in the mixture. It represents the concentration of $Cu^+$ and $Zn^{+2}$ ions released in a balanced mixture of cuprous oxide, cuprous thiocyanate and zinc oxide, being exposed to an aqueous solution in constant renewal (washing). The evolution of the cuprous ions ($Cu^+$) follows from the chart, as well as the total amount of cuprous and zinc ions in a mixture that is constantly exposed to balance with an aqueous solution.

The present invention consists of a biocide composition of active powders that includes atleast one copper salt and at least one zinc salt, more preferably including at least two copper salts and at least one zinc salt or at least one copper salt and at least two zinc salts, in order for the molar ratio between the total amount of copper salts and the total amount of zinc salts to be within the range that goes from 10:1 to 1:1 and each copper and zinc salt, by themselves, have a solubility constant (Kps) within the range that goes from a value equal or greater than $1*10^{-20}$ until a value equal to or less than $9*10^{-6}$.

The copper and zinc salts considered in the present invention may be any sort of organic and inorganic copper and zinc salt that have a solubility constant within the range that goes from a value greater than or equal to $1*10^{-20}$ until a value equal to or less than $9*10^{-6}$. Nonetheless, the preferably considered copper and zinc salts are listed in Charts No. 1 and Chart No. 2, respectively.

CHART NO. 1

Copper salts with their respective solubility constant and classification according to their Kps value.

| Copper Based Salts | Solubility Constant in Aqueous Solution (Kps) | Group |
|---|---|---|
| Copper (I)Chloride | $1*10^{-6}$ | A |
| Copper (II)Iodate | $1.4*10^{-7}$ | A |
| Copper(I)Pyrithione | $4*10^{-8}$ | A |
| Copper (II)Oxalate | $4*10^{-10}$ | A |
| Copper (II)Carbonate | $1.4*10^{-10}$ | A |
| Copper(I)Phthalocyanine | $3*10^{-12}$ | B |
| Copper(I)Iodide | $1.1*10^{-12}$ | B |
| Copper(I)Thiocyanate | $1.6*10^{-13}$ | B |
| Copper(II)Thiocyanate | $4*10^{-14}$ | B |
| Copper (I)Hydroxide | $1*10^{-14}$ | B |
| Copper(I) Oxide | $2*10^{-15}$ | B |
| Copper(II)Ferrocyanide | $1.3*10^{-16}$ | C |
| Copper (II)Hydroxide | $4.8*10^{-20}$ | C |
| Copper (I)Cyanide | $3*10^{-20}$ | C |
| Copper (II)Oxide | $2.2*10^{-20}$ | C |

CHART NO. 2

Zinc salts with their respective solubility constant and classification according to their Kps value.

| Zinc Based Salts | Solubility Constant in Aqueous Solution (Kps) | Group |
|---|---|---|
| Zinc Iodate | $3.9*10^{-6}$ | A |
| Zinc Tartrate | $2.2*10^{-6}$ | A |
| ZincPyrithione | $2.5*10^{-8}$ | A |
| Zinc Oxalate | $1.4*10^{-9}$ | A |
| Zinc Oxide | $3.9*10^{-10}$ | A |
| Zinc Carbonate | $1.4*10^{-11}$ | B |
| Zinc Cyanide | $4*10^{-16}$ | C |

In Chart No. 1 and Chart No. 2 it can be seen that the copper and zinc salts have been classified according to their solubility constant value into three groups, named A, B and C, which have been defined in conformity with the following ranges of solubility constants:

Group A: salts with a Kps within a range that goes from a value greater than $9*10^{-11}$ until a value equal to or less than $9*10^{-6}$.

Group B: salts with a Kps within a range that goes from a value greater than $9*10^{-16}$ until a value equal to or less than $9*10^{-11}$.

Group C: salts with a Kps within a range that goes from a value greater than or equal to $1*10^{-20}$ until a value equal to or less than $9*10^{-16}$.

Additionally, keeping present that the release of the biocide agent of a given salt is defined by the value of its solubility constant, we have classified the biocide compositions of the present invention according to their action capacity, for which the Impact Index is defined as:

High Impact and Short Life (HISL):
Composition that contains high concentration and fast release of the biocide ions at the beginning of the utilization of the product.

Medium Impact and Medium Life (MIML):
Composition that contains a medium concentration of biocide ions at the beginning of the utilization of the product and a longer duration of the biocide effect in time.

Controlled Release and Long Life (CRLF):
Composition that contains a smaller initial concentration of biocide ions, but a slow release and a great duration of the biocide effect in time.

In turn, the impact indexes have been classified with the following numeric values:
HISL: Impact index greater than or equal to 80.
MIML: Impact index less than 80 and greater than or equal to 60.
CRLF: Impact index less than 60.

In order to accomplish linking the impact indexes of the salts to be used in the composition, a numeric value has been assigned to each sort of salt according to groups A, B and C, this is how salts belonging to group A are assigned the value 100, the salts from group B the value 50 and the salts from group C the value 25. The impact index of the composition is determined by the sum of the products that result from multiplying the molar fraction of each salt by the numeric value assigned according to the group to which each salt belongs to, for example there is a composition that included:

20% molar of a type A salt
40% molar of a type A salt
40% molar of a type B salt
Thus the impact index would be:

0.2*100+0.4*100+0.4*50=80

Because the impact index obtained is equal to 80, this means that this corresponds to a composition intended to be used in a high impact and short life application.

This way it has been established, that the selection of copper and zinc salts forming the biocide composition of the present invention, depends on the use that the biocide composition will have, because the impact index of said composition must previously be established and once said impact index is determined, the salts to be used in the composition are selected. The following formulas that relate the impact index with the value assigned to each salt group and with the molar ratio of each salt to be included in the composition are described in a general form:

High Impact and Short Life (HISL):

(0.05 to 1.0)*100+(0 to 1.0)*50+(0 to 1.0)*25>=80   (I)

Medium Impact and Medium Life (MIML):

(0.01 to <0.8)*100+(0 to 1.0)*50+(0 to 1.0)*25<80 y>=60   (II)

Controlled Release and Long Life (CRLF):

(0.01 to <0.6)*100+(0 to 1.0)*50+(0 to 0.35)*25<60   (III)

Equation (I) indicates that in order to obtain a composition of high impact and short life, said composition must contain 5 to 100% of salt belonging to group A, 0 to 100% of salt from group B, and 0 to 100% of salt from group C, and the percentages of each salt group should be such, that the sum (impact index) of the products that result from multiplying said molar fraction of each salt group, by the numeric value assigned according to the group to which each salt belongs to, must be greater than or equal to 80. In turn, equation (II) indicates that in order to obtain a composition of medium impact and medium life, said composition must contain from 1 to <80% of salt from group A, 0 to 100% of salt from group B, and 0 to 100% of salt from group C, and the percentages of each salt group should be such, that the sum (impact index) of the products that result from multiplying said molar fraction of each salt group, by the numeric value assigned according to the group to which each salt belongs to, must be greater than or equal to 60 and less than 80. Similarly, equation (III) indicates that in order to obtain a composition of controlled release and long life, said composition may contain from 1 to <60% of salt from group A, 0 to 100% of salt from group B, and 0 to 35% of salt from group C, and the percentages of each salt group should be such that the sum (impact index) of the products that result from multiplying said molar fraction of each salt group by the numeric value assigned according to the group to which each salt belongs to, must be less than 60. Bearing in mind that by indicating "salt from group" this could be one or more copper salts, one or more zinc salts, or mixtures of both, as long as each and all of the salts belong to the same group.

Additionally, it must be kept present that the composition must always contain at least two copper salts and at least one zinc salt or at least one copper salts and at least two zinc salts, in order for the molar ratio between the total amount of copper salts and the total amount of zinc salts to be within the range that goes from 10:1 to 1:1.

The type of salt used in the composition allows, through its solubility constant, to determine the maximum concentration of available ions for biocide effects in the composition. In turn, the need of biocide agents is, in many cases, defined by the value of Minimum Inhibitory Concentration (MIC), which is characteristic of each microorganism, biocide agent, environmental conditions, crystal structure and others. For example, the MIC value for copper in the Subtilis bacteria has been determined to be $4*10^{-8}$ molar of $Cu^+$ ions, while this value is $35*10^{-8}$ molar for the *Staphylococcus aureus*.

The solubility product (Kps) is the product of the molar concentrations (at balance) of the constituent ions, each one raised to the power of the stoichiometric coefficient in the balance equation.

$$X_m Y_n \leftrightarrow mX^{n+} + nY^{m-}$$

Where X represents a cation (metallic ion), Y an anion and m and n are their respective stoichiometric indexes (valences). Thus, attending to their definition, their solubility product will be:

$$Kps = [X^{n+}]^m [Y^{m-}]^n$$

A greater Kps value indicates that the solubility is greater, as opposed to a smaller value being less soluble. That is to say less ions of the species that form the salt are free or in their ionic state. The solubility of a salt may be affected if there exists another salt in the system that has a common ion, solubility will diminish, which is known as the common ion effect.

The solubility values (concentration of free ions) are expressed in moles of solute by liter of solution.

Once the biocide composition of active powders is obtained, it is mixed with a polymer in order to obtain the final biocide composition. The polymer may be any sort of polymer, but preferably the chosen polymer will be polyethylene, polypropylene, polyester, PVC, polyamide, ABS (acrylonitrile butadiene styrene), polycarbonate.

Fabrication Method of the Composition

The composition is produced by thickly mixing the components together in order to obtain a homogenous distribution of the different salts in the powder mixture. The mixing can be done in a continuous mixer or batch. The mixture is henceforth called "active powders". The particle size of the used salts must approximately be less than 2 microns, being preferably smaller than approximately 1 micron. We have found that at least one of the salts used in the mixture must have a particle size approximately smaller than 0.5 microns. This allows a better arrangement of the active ingredients in order for them to cover more surface, leave less intergranular spaces and optimize the surface area/volume ratio of the active powders.

The mixing should preferably be done in an oxygen free atmosphere in order to prevent possible or potential oxidative reactions and decomposition reactions of the reagents. The oxygen free atmosphere can be achieved by cleaning the system with nitrogen, argon, helium or a mixture of these gases. The mixing temperature must be controlled in order for it to be approximately less than 50° C. In some cases, chemical compounds that help the de-agglomeration of the particulate material should additionally be used, for instance acetone.

The obtained mixture of active powders and the polymer are mixed, and the polymer is able to be either in solid phase or liquid phase. Given the case that the polymer is in solid phase, the mixing is to be done in a continuous mixer or batch in a controlled oxygen free environment.

In turn, given the case that the polymer is in liquid phase, the mixing with the active powder should be done in a continuous mixer or batch in an oxygen free atmosphere; where the mixing temperature should be controlled in order for it to be at least 10° C. higher than the solid-to-liquid phase change temperature, in order to prevent the formation of clumps. At any given moment the system has to be kept free of oxygen. In the case of using a liquid dispersant, it could completely evaporate during this stage.

Once the mixture is finished, the polymer with the copper and zinc salts incorporated into its structure is ready to be processed in order to obtain its final form. The process may be extrusion (cold or hot), injection (cold or hot), foaming, gelation, stamping or any other process. During the transformation process of the polymer with active powders there may be more polymer added in order to dilute the concentration of active powders within the mixture. The concentration of active powders in the final product may approximately be within 0.1% and 70%, and the quantity of the polymer goes approximately from 30% to 99.9%. The pressure of the mixing process may be kept controlled within approximately 0.1 and 100 atmospheres.

The final product may take the form of yarns, pellets, plaques, non-woven, sheets, films, gels, adhesives, fibers, foams, resins, emulsions, paints, suspensions, and others, using the traditional transformation processes of polymers.

Applications of End Product:

Depending on the form of the end product the applications the product may have are as follows:

Yarn: It is used in the production of fabrics and stockinettes, looms, crochet, and clothes obtained from these materials, for human, animal, home, office and hospital use.

Filaments: The extrusion of polymers into filaments is useful for the production of brushes, brooms, carpets, ropes, and others.

Plastic Laminates: It includes all sort of products made with polymer laminates, extruded or molded in all sorts of forms (such as trays, cups, packing material, shower curtains, bath covers, trashcans, films for coating, handle, containers, cleaning equipments, electrical goods, furniture, filters).

Non-woven Fabrics: It includes all sort of products made with non-woven fabrics, such as: medical uniforms, hospital material, masks, dressings, bandages, diapers, sanitary towels, cleaning cloths, filling material, covering, filters, care-giving products for persons, animals, environment.

Foam: Corresponds to foamed polymers, such as sponges, which use noise, impact and smell absorbents; filters, protectors, and others.

Adhesives: All sort of synthetic adhesive is considered.

Gels, Emulsions and/or Creams: All sort of compounds with a chemical structure of a gel or emulsion is considered.

Resins: Includes all sort of products based on resins, such as melamine and ureic resins, and others.

Paints and/or Varnishes and/or polymeric suspensions: Includes, for instance, paints, pastes, and suspensions of the sort of nail polish.

The composition that contains high concentration and fast release of biocide ions are applicable, for instance in dressings, creams, bandages, non-woven fabrics, that is to say, in products that will be used for a brief time or of short life.

The compositions that contain a medium concentration of biocide ions at the beginning of the use of the product and a greater duration of the biocide effect in time are applicable, for instance in textile yarns of polyester, nylon, polyamide, polypropylene, and the polymer products are injected, molded or extruded; in resin products such as foams, gels, paints, that is to say in products that will be used for several months or years.

The compositions that contain a smaller initial concentration of biocide ions, but a slow release and a great duration of the biocide effect in time are applicable, for instance in yarns with textile and non-textile applications; applications in woods either as impregnation, resins for surfaces melamine, ureic or formic surfaces, paints, varnishes; and surfaces made of polymers obtained by injection, extrusion, molding and others.

EXAMPLES

1. Polyethylene Application in Aquaculture Tubes

Using a mixture of copper salts, cupric carbonate and cupric oxide, respectively, and zinc salt, and zinc carbonate. It has been determined that the use of zinc salts produces a synergistic effect with the copper salts. The polymer may be polyethylene, polypropylene, polyester, PVC, polyamide, ABS or other polymer.

The example was performed with polyethylene.

Kps Values
    Cupric Carbonate: $1.4 \times 10^{-10}$
    Cupric Oxide: $2.2 \times 10^{-20}$
    Zinc Carbonate: $1.4 \times 10^{-11}$ Formulation 1:

|  | % Molar | % Weight |
|---|---|---|
| Cupric Carbonate | 70 | 74.3 |
| Cupric Oxide | 17 | 11.6 |
| Zinc Carbonate | 13 | 14.0 |

The molar ratio of copper salts to zinc salts is 6.7.
Impact Index=81

The total initial concentration of available cupric ions $(Cu^{+2})$ will be $1.1 \times 10^{-5}$ and of zinc ions $(Zn^{+2})$ will be $1.1 \times 10^{-6}$. The available quantity is given by the contribution of each salt, their molar percentage in the salt mixture and the common cation effect in the system. This way, the calculations using the Kps values are as follows:

$$CuCO_3 = Cu^{+2} + CO_3^{-2} \qquad (1)$$

Kps11=$1.4 \times 10^{-10}$
(X+Y) (X+Z)

$$CuO = Cu^{+2} + O^{-2} \qquad (2)$$

Kps21=$2.2 \times 10^{-20}$
(X+Y) (Y)

$$ZnCO_3 = Zn^{+2} + CO_3^{-2} \qquad (3)$$

Kps31=$1.4 \times 10^{-11}$
(Z) (X+Z)

The Kps values are the solubility products of the salts (Chart 1 and Chart 2).

(X) represents the concentration of ions $Cu^{+2}$ and $CO_3^{-2}$ released in reaction 1 at balance.

(Y) represents the concentration of $Cu^{+2}$ and $O^{-2}$ released in reaction 2 at balance.

(Z) represents the concentration of ions $Zn^{+2}$ and $CO_3^{-2}$ in reaction 3 at balance.

Writing the equations:

$$Kps11=(X+Y)(X+Z)$$

$$Kps21=(X+Y)(Y)$$

$$Kps31=(Z)(X+Z)$$

By solving these equations it is obtained (X+Y) that corresponds to the total concentrations of ions $Cu^{+2}$, and (Z) to the concentration of ions $Zn^{+2}$. The values are $1.1*10^{-5}$ and $1.1*10^{-6}$, respectively.

Formulation 2:

|  | % Molar | % Weight |
|---|---|---|
| Cupric Carbonate | 17 | 22.6 |
| Cupric Oxide | 70 | 59.9 |
| Zinc Carbonate | 13 | 17.6 |

The molar ratio of copper salts to zinc salts is 6.7.
Impact Index=41

The initial concentration of available cupric ions will be $2*10^{-6}$ and of zinc ions will be $4.9*10^{-7}$. The available quantity is given by the contribution of each salt, their molar percentage in the salt mixture and the common cation effect in the system. It is solved in identical fashion as was explained in formula 1.

The salts are mixed in an oxygen free environment until a homogenous mixture of powders is obtained. The mixture is then mixed with polyethylene pellets and then passed through a sprayer. The active powder and polymer mixture is carried to a rotomolding process where the tubes are produced. The quantity of active powders in the final product is of 5% and the quantity of polyethylene in the mixture is of 95%.

From this example, if the needs of application are of the HISL sort, the molar ratio of cupric oxide/cupric carbonate is 0.25 (Formulation 1), if the need is of the CRLF sort, the ratio of copper salts is 4.

Biocide Activity Index[1] in *Escherichia Coli*:

| Freshly made plaques | |
|---|---|
| Formulation 1 | 100 |
| Formulation 2 | 60 |

[1] The Biocide Activity Index is the ratio between the disposal of bacteria in the test sample and the control sample. The Biocide Activity Index of the control sample is equal to 100.

Where formulation 1 represents the control sample, formulation 1 will be the maximum rate of disposal of bacteria and for all purposes it is equivalent to 100. Formulation 2 will be evaluated in respect of formulation 1, therefore that the value is 60 means that formulation 2 only disposed 60% of the bacterias that formulation 1 disposed of.

Plaques are submerged in water for 1,600 hours. The time of residence of water is 5 min, after those 5 minutes, the water is changed completely. The plaques are submerged in water, because in doing so the formulation with more soluble salts will experience a loss of these salts by contact with water, greater than the formulation with less soluble salts and that will make the Biocide Activity Index change after many hours, if it stays in a water container where every 5 minutes the water is changed completely. The new Biocide Activity Index values for each of the formulations are as follows:

| Formulation 1 | 100 |
|---|---|
| Formulation 2 | 125 |

2. Non Woven Fabrics Application

By using the mixture of copper salts, cuprous thiocyanite and cuprous oxide, respectively, and zinc salt, zinc oxide in non woven fabrics may be made of polypropylene, polyester or other polymer.

Kps Values
  Cuprous Thiocyanite: $1.6*10^{-13}$
  Curpous Oxide: $2*10^{-15}$
  Zinc Oxide: $3.9*10^{-10}$ Formulation 3:

|  | % Molar | % Weight |
|---|---|---|
| Cuprous Oxide | 47 | 57.1 |
| Cuprous Thiocyanite | 18 | 18.6 |
| Zinc Oxide | 35 | 24.3 |

The molar ratio between copper salts and zinc salts is 1.9.
Impact Index=68

The initial concentration of available cuprous ions will be $2*10^{-7}$ and $9*10^{-6}$ of zinc ions. The available quantity is given by the contribution of each salt, their molar percentage in the salt mixtures and the common cation effect in the system.

The salts are thickly mixed and a hot stream of argon, helium or nitrogen (free of oxygen) is passed through the bed containing the mixture in order to remove humidity. The particle size of the cuprous oxide is approximately less than 1 micron, the particle size of zinc oxide is approximately less than 0.1 micron and the particle size of cuprous thiocyanite is approximately 5 microns. This difference in particle size allows for a better surface packaging.

The dry salts are cooled and taken to a melting mixer (worm) where polypropylene is fed as the polymer is melted and mixed with the dried salts until a homogenous paste is formed. The paste is fed into the non woven forming table. The entire process is performed in an oxygen free environment. The fabrics may have a weight from 15 g/m² to 300 g/m².

The percentage of salts in this fabric is within the range that goes from 2% to 15%. As an example, a fabric was prepared with 2% and one with 15%, with the polypropylene content 98% and 85%, respectively.

Biocide Activity Index in *Staphylococcus Aureus*
  Non-Woven Fabric without Active Agents: 100
  Non-Woven Fabric with Active Agents: 800

3a. Textile Yarns

Using the mixture of copper salts, cuprous oxide and cupric oxide, and zinc salts, zinc oxide and zinc carbonate, in yarns of polyester, nylon, polyamid, polypropylene or other polymer. The zinc salts, besides their biocide and synergistic property with copper salts, serve the textile yarns with other benefits, such as the oxide acting as a UV filter and the carbonate as a fire retardant.

Kps Values

Cuprous Oxide: $2*10^{-15}$

Cupric Oxide: $2.2*10^{-20}$

Zinc Carbonate: $1.4*10^{-11}$

Zinc Oxide: $3.9*10^{-10}$

Formulation 4a:

|  | % Molar | % Weight |
|---|---|---|
| Cuprous Oxide | 60 | 68.7 |
| Curpic Oxide | 5 | 3.2 |
| Zinc Carbonate | 15 | 15.1 |
| Zinc Oxide | 20 | 13.1 |

The molar ratio of copper salts to zinc salts is 1.9.

Impact Index=59

The initial concentration of available cuprous ions will be $6.8*10^{-6}$, the concentration of cupric ions will be $3*10^{-11}$, and of zinc ions will be $1.9*10^{-6}$. The available quantity is given by the contribution of each salt, their molar percentage in the salt mixture and the common cation effect in the system.

The particle size of the cupric oxide and zinc carbonate salts is of the order of 2 microns and in the case of the cuprous oxide and zinc oxide is less than approximately 0.5 microns. As it has been said before, this difference of particle size allows for a better distribution and accommodation of them on the yarn surface. Besides, for a better performance the ratio between the diameter of the yarn filaments and the maximum diameter of the particles has to be at least approximately equal to 5.

The copper salts are mixed until a homogenous distribution is achieved in a V-Blender agitator with an intensifying bar in an oxygen free atmosphere. The mixture is fed with a polyester in a heated twin mixer at approximately 260° C. As the mixture moves forward the polymer is melted and mixed with the salts until a liquid and homogenous dispersion state is achieved. All of this is done in an oxygen free environment in order to prevent oxidations. The mixture is extruded in cylinders of 3×2 mm and cooled instantly by falling in an stirred medium that is kept at approximately 0° C.

The pellets are taken into a polyester polymerization reactor that is kept at approximately 270° C. where they are added, melted and mixed. When this happens, the biocide particles are kept trapped in the polymer net that is being formed. It is not intended nor expected that some sort of chemical bond between the active particles and the polymer is formed. The reactor polymer is injected in order to form the filaments with the yarn. Above the reactor, an inert atmosphere is set up in order to prevent oxidations on the surface of the reactor.

The yarn is formulated this way to present a greater activity than the yarns of cuprous oxide and zinc oxide at the same concentration of copper and zinc ions (author's previous patent), which is evidence of the synergistic activity of having different salts in a same metal. The percentage of active powders in the yarn may go from 0.5 to 5%, whereas 1% is desirable. In the case of polyester, the percentage of it in the mixture goes from 99.5% to 95%, where a content of 99% is desirable.

Biocide Activity Index in *Staphylococcus Aureus*

| Yarn without actives | 20 |
|---|---|
| Threads (cuprous oxide + zinc oxide) | 100 |
| Threads (formulation 4a) | 140 |

3b. Textile Yarns

Using a mixture of copper salt, cuprous thiocyante, and zinc salts, zinc oxide and zinc carbonate in yarns of polyester, nylon, polyamide, polypropylene or other polymers. The zinc salts, besides their biocide and synergistic properties with copper salts, serve other benefits to the textile yarn, because the oxide acts as a UV filter and the carbonate as a fire retardant. Besides, this allows for the creation of yarns of white color without the need of using dye.

Kps Values

Cuprous Thiocyanate: $1.6*10^{-13}$

Zinc Carbonate: $1.4*10^{-11}$

Zinc Oxide: $3.9*10^{-10}$

Formulation 4b:

|  | % Molar | % Weight |
|---|---|---|
| Cuprous Thiocyanate | 75 | 78.6 |
| Zinc Carbonate | 10 | 10.8 |
| Zinc Oxide | 15 | 10.5 |

The molar ratio of copper salts to zinc salts is 3.0.

Impact Index=58

The initial concentration of available cuprous ions will be $2.9*10^{-5}$ and of zinc ions will be $1.7*10^{-6}$. The available quantity is given by the contribution of each salt, their molar percentage in the salt mixture and the common cation effect in the system.

The particle size of the cuprous thiocyanate and zinc carbonate is of the order of 2 microns and the one of zinc oxide is approximately less than 0.5 microns. As it has been stated previously, this difference in particle size allows for a better distribution and accommodation of them on the yarn surface. Also, for a better performance the ratio between the diameter of the yarn filaments and the maximum particle diameter must be at least equal to 5.

The copper and zinc salts are mixed until a homogenous distribution is achieved in a V-Blender agitator with intensifying bar in an oxygen free atmosphere. The mixture is fed along with polyester in a heated twin mixer at approximately 260° C. As the mixture moves along the polymer, it is melted and mixed with the salts until a liquid and homogenous dispersion state is achieved. All of this is done in an oxygen free ambient environment in order to avoid oxidations. The mixture is extruded into cylinders of 3×22 mm and cooled instantly by falling into an agitated medium that is kept approximately at 0° C.

The pellets are taken to the polyester polymerization reactor that is kept approximately at 270° C. where they are melted and mixed. When this happens, the biocide particles are kept trapped in the polymer net that is being formed. It is not intended nor expected that some sort of chemical bond between the active particles and the polymer takes place. The reactor polymer is injected in order to form the filaments with the yarn. Over the reactor, an inert atmosphere is set up in order to prevent oxidations on the surface of the reactor.

The yarns formulated this way are of white color and have a similar activity to those of Formulation 4. The percentage of active powders in the yarn may vary from 0.5 to 5%, where 1% is desirable.

Biocide Activity Index in *Staphylococcus Aureus*

| | |
|---|---|
| Yarn without actives | 20 |
| Threads (Formulacion 4b) | 130 |

4. Melaminic, Ureic and Formaldehyde Covering

Using a mixture of copper salt, cuprous thiocyanate, and zinc salts, zinc oxide and zinc carbonate for a melaminic formulation of resins with biocide properties intended to be applied in post-formed panels. These salts were chosen because of having a solubility constant between $1*10^{-10}$ and $1*10^{-14}$ and because of being an almost white color, which allows obtaining white melamine without the need of adding dyes that could alter the biocide activity.

Kps Value
  Cuprous Thiocyanate: $1.6*10^{-13}$
  Zinc Carbonate: $1.4*10^{-11}$
  Zinc Oxide: $3.9*10^{-10}$
Formulation 5:

| | % Molar | % Weight |
|---|---|---|
| Cuprous Thiocyanate | 89 | 91.6 |
| Zinc Oxide | 6 | 4.14 |
| Zinc Carbonate | 4 | 4.25 |

The molar ratio between copper and zinc salts is 5.7
Impact Index=50

The chosen composition is such that the concentrations of free copper and zinc ions are in the same order of magnitude, $1*10^{-7}$, given the solubility constants and the common ion effect.

The salts are thickly mixed in order to obtain a homogenous mixture. The powders are then mixed with a melamine solution at 40% in melamine weight the rest being water, the quantity of active solids may be within the range that goes from 0.5% a 5%. This mixture is agitated at high revolutions in a turbo-mixer in order to assure a good mixing and that no clumps remain. The solution is passed through a sieve with a mesh opening of 37 microns in order to eliminate clumps. A needed dispersant is added.

For the application of the solution, a paper of 80 grams/m2 caliber, onto which ureic resin may or may not have been deposited, is passed through a melamine solution with active agents. Afterwards it is passed through rollers in order for the impregnation to be of the order of 70 g/m² of melamine solution on the paper with up to 200 g/m² of melamine solution carried on the paper. The impregnated paper is dried at approximately 110° C. Once the paper is dried it is applied onto the wood and glued to it, by heating it to approximately 150° C. and at approximately 100 bar. The percentage of active powders is of 2% and the percentage of melamine is of 98%.

Biocide Activity Index for 2% Active Powders in *Escherichia Coli*

| | |
|---|---|
| Melamine withou actives | 100 |
| Melamine with actives | 160 |

The same process may be performed by replacing melamine with ureic, formaldehyde or other resin, and/or jointly, namely the active powders may disperse in each and every phase.

5. Varnish

Using a mixture of copper salts, cuprous thiocyanate, cuprous oxide, copper oxalate, and zinc salts, zinc oxide and zinc oxalate for the varnish formulation with biocide properties intended to be used in nails, animal hooves, surfaces, paints. These salts were chosen because they have solubility constants lower than $1*10^{-15}$, in addition to presenting a wide range of salts and, with this, covering a greater range of microorganisms.

Kps Values
  Cuprous Thiocyanate: $1.6*10^{-13}$
  Cuprous Oxide: $2*10^{-15}$
  Copper Oxalate: $4*10^{-10}$
  Zinc Oxide: $3.9*10^{-10}$
  Zinc Oxalate: $1.4*10^{-9}$
Formulation 6:

| | % molar | % weight |
|---|---|---|
| Cuprous Thiocyanate: | 63 | 58.7 |
| Cuprous Oxide: | 13 | 14.3 |
| Copper Oxalate: | 9 | 10.5 |
| Zinc Oxide: | 11 | 6.9 |
| Zinc Oxalate: | 4 | 9.6 |

The molar ratio between copper salts and zinc salts is 5.7.
Impact Index=62

The salts are thickly mixed until a uniform composition is achieved. The salts must have a particle size approximately lower than 10 microns, with at least two particles, one of zinc and one of copper, being of a particle size approximately lower than 1 micron.

The mixed salts are dispersed in a solution containing dissolver polystyrene, or in acrylic solutions. When applied, the solvent evaporates and the polymer with the active powder incorporated to its structure remains. The percentage of active powders is of 4% and the percentage of polystyrene and/or acrylic solution is of 96%.

Biocide Activity Index of Varnish, with 4% Active Powders in *Candida Albicans*

| | |
|---|---|
| Varnish without actives | 100 |
| Varnish with actives | >260 |

6. Fibers and Plaques for Pisciculture

Using a mixture of copper salts, copper pyrithione, copper thiocyanate, cuprous oxide, y zinc salts, zinc pyrithione and zinc carbonate for the formulation of fibers, molded plaques, ropes, floaters, coating with biocide properties and antifouling for the use in pisciculture and marine or high humidity environments incorporated may it be in polyethylene, polypropylene, polyester, polycarbonate, ABS or other polymers.

Kps Values:
  Copper Pyrithione: $4.8*10^{-8}$
  Copper Thiocyanate: $1.6*10^{-13}$
  Cuprous Oxide: $2*10^{-15}$
  Cupric Oxide: $2.2*10^{-20}$
  Zinc Pyrithione: $2.5*10^{-8}$
  Zinc Carbonate: $1.4*10^{-11}$
Formulation 7:

| | % molar | % weight |
|---|---|---|
| Copper Pyrithione: | 10 | 21.10 |
| Copper Thiocyanate: | 15 | 12.18 |
| Cuprous Oxide: | 15 | 14.33 |

-continued

|  | % molar | % weight |
|---|---|---|
| Cupric Oxide: | 35 | 18.59 |
| Zinc Pyrithione: | 10 | 21.23 |
| Zinc Carbonate: | 15 | 12.58 |

The molar ratio between copper salts and zinc salts is 3.0.
Impact Index=51

In this case, the homogenous mixture of powders is done in an inert environment. The powders are mixed with the polymer and are passed through a sprayer if needed in order to obtain a homogenous mixture. Afterwards, depending on the process, it follows to obtain a working form. If this process is extrusion, a concentrated pellet with active powders is prepared and added as needed. If it is by rotomolding, the polymer and active powders are mixed when the mold is loaded, and both are sprayed. At all times, it should be checked that the environment is kept free of oxygen if the temperatures exceed approximately 50° C. The load of active powders is within the range of 1-10%, where 4% is most desirable. The example was prepared for 4% of active powders and 96% of polyethylene.

Biocide Activity Index for 4% of Active Powders in *Escherichia Coli*

| Base Preparation without actives | 100 |
|---|---|
| Base Preparation with actives | >350 |

7. Creams

Using the mixture of copper salts, cuprous thiocyanate, cuprous chloride, cupric iodate, zinc oxide and zinc iodate for the formulation of creams with biocide properties intended to be applied in animals, such as cow udder, skin and surfaces. These salts were chosen because in addition to copper and zinc, the cations of chloride and iodate salts serve beneficial actions in the care and sterilization of skin and surfaces. They are ions of fast release, over 90%, and they have a solubility constant over $1*10^{-10}$ and over 65% solubility constants are greater than $1*10^{-7}$.

Kps Values
  Cuprous Thiocyanate: $1.6*10^{-13}$
  Copper Chloride: $1*10^{-6}$
  Cupric Iodate: $1.4*10^{-7}$
  Zinc Oxide: $3.9*10^{-10}$
  Zinc Iodate: $3.9*10^{-6}$ Formulation 8:

|  | % molar | % weight |
|---|---|---|
| Cuprous Thiocyanate: | 28 | 15.71 |
| Copper Chloride: | 5 | 2.29 |
| Cupric Iodate: | 25 | 47.71 |
| Zinc Oxide: | 30 | 11.29 |
| Zinc Iodate: | 12 | 23.01 |

The molar ratio between copper salts and zinc salts is 1.4.
Impact Index=86

A hydrogel is prepared, that may contain polyvinyl alcohol and gelatin. A hydrogel based on surfactants and thickening agents may also be used. The salts are mixed and dispersed in the gel until a solution is obtained. The load of salts is within the order of 1.000 to 10.000 ppm of copper and the corresponding quantity of zinc ions. The example is prepared for a content of 1% of active powders and 99% base gel.

Biocide Activity Index in *Escherichia Coli*

| Base Cream: | 100 |
|---|---|
| Cream with Formula: | >400 |

8. Wood Protection

Using the mixture of copper salts, copper pyrithione, copper carbonate, cuprix oxide, and zinc salts, zinc pyrithione and zinc carbonate for creams with biocide properties for wood impregnation, paints and surface protection. These salts were chosen because their anions can abandon the surface (oxygen and carbon) due to the conditions to which the salts are exposed without affecting the biocide property.

Kps Values
  Copper Pyrithione: $4.8*10^{-8}$
  Copper Carbonate: $1.4*10^{-10}$
  Cupric Oxide: $2.2*10^{-20}$
  Zinc Pyrithione: $2.5*10^{-8}$
  Zinc Carbonate: $1.4*10^{-11}$ Formulation 9:

|  | % molar | % weight |
|---|---|---|
| Copper Pyrithione | 10 | 22.11 |
| Copper Carbonate: | 10 | 8.65 |
| Cupric Oxide: | 45 | 25.04 |
| Zinc Pyrithione: | 10 | 22.24 |
| Zinc Carbonate: | 25 | 21.96 |

The molar ratio between copper and zinc salts is 1.9.
Impact Index=54

The salts are mixed with a water soluble polymer, such as hydroxyethylcellulose, latex powders, ethyl cellulose, cellulose ether, or water-soluble resins. The soluble polymer serves as a carrier in order to incorporate formulation 9 into the wood and migrate into the cells afterwards.

In-vitro testing of the activity of the formula have been carried out by superficially impregnating wood with the polymer and with the polymer of formulation 9. Active powder impregnation between 0.01-1%, desirable 0.2%. The example is prepared for a content of 1% of active powders and a content of 99% of hydroxyethyl cellulose at 20% water weight.

Biocide Activity Index in Fungus

| Alcohol impregnated wood | 100 |
|---|---|
| Wood impregnated with formula 9 | >250 |

The invention claimed is:
1. An antibacterial and antifungal biocide composition for inclusion in a polymer-based product consisting of:
   a first copper-based salt;
   a second zinc-based salt; and
   a third salt, said third salt being either copper-based or zinc-based;
   wherein
      the number of moles of copper salts in said composition is from 1 to 10 times the number of moles of zinc salts in said composition;
      at least one of said first, second, or third salts has a particle size of no greater than 0.5 microns;
      said salts are selected so as to collectively have solubility constants (Ksp) in the range of 1*10-20 to 9*10-6;

at least 1% by weight of the salts in said composition have a Ksp in the range of $9*10-11$ to $9*10-6$;

the composition consists of three mole fractions where the fractions are selected such that a first mole fraction (M1) of said salts has a Ksp in the range of from $9*10-11$ to $9*10-6$, a second mole fraction (M2) of said salts has a Ksp in the range of $9*10-11$ to $9*10-16$, and a third mole fraction (M3) of said salts has a Ksp in the range of $9*10-16$ to $1*10-20$; M1+M2+M3=the entire composition; and the composition conforms to the following formula:

$$100*M1+50*M2+25*M3>=80.$$

2. The biocide composition of claim 1, wherein 1 to <80% of the moles in the composition has a Ksp in the range of $9*10-11$ to $9*10-6$.

3. The biocide composition of claim 1, wherein 1 to <60% of the moles have a Ksp in the range of $9*10-11$ to $9*10-6$, and less than 35% of the moles have a Ksp in the range of $1*10-20$ to $9*10-16$.

4. A method for formulating an antibacterial and antifungal controlled release biocide polymer-incorporated yarn comprising the steps of:

mixing three salts in an oxygen-free environment, in a temperature range of 10-50 C, using a continuous mixer until the particles size of the salts is below a threshold value, said three salts selected to result in controlled and time-distributed release of biocides over an extended duration, including;

a first copper-based salt;

a second zinc-based salt; and a third salt, said third salt being either copper-based or zinc-based;

at least one of said salts selected to have a solubility constant from $9*10^{-11}$ to $9*10^{-6}$;

at least one of said salts selected to have a solubility constant from $9*10^{-16}$ to $9*10^{-11}$; and at least one of said salts selected to have a solubility constant from $9*10^{-16}$ to $9*10^{-20}$;

adding a polymer to form a resultant mixture so said mixture comprises 30-99.99% polymer, said polymer selected from the group consisting of polyethylene, polypropylene, polyester, PVC, polyamide, ABS (acrylonitrile butadiene styrene), and polycarbonate; and incorporating by extrusion or injection said resultant mixture into a yarn suitable for a garment material;

wherein said resultant mixture results in controlled time-distributed release of biocide ions.

5. The method of claim 4, where said biocide is directed to combating *E. coli*.

6. The method of claim 4, where said biocide is directed to combating *staphylococcus*.

7. The method of claim 4, where said biocide is directed to combating fungus.

8. The method of claim 4, where said polymer is in a liquid phase at the time of combining with said salts.

9. The method of claim 4, wherein at least 5% of all salt by weight has a solubility constant in the range of $9*10^{-11}$ to $9*10^{-6}$.

10. The method of claim 4, wherein said threshold value is 2 microns.

11. The method of claim 4, wherein at least one salt has a particle-size less than or equal to 0.5 microns.

12. The method of claim 4, wherein additional said polymer is added during the process to disperse or mix the salts.

13. The method of claim 4, wherein said threshold value is 0.5 microns.

14. The method of claim 4, where said biocide is directed to combating bacteria.

15. The method of claim 4, further including the step of incorporating said yarn into a garment.

* * * * *